Figure 1:
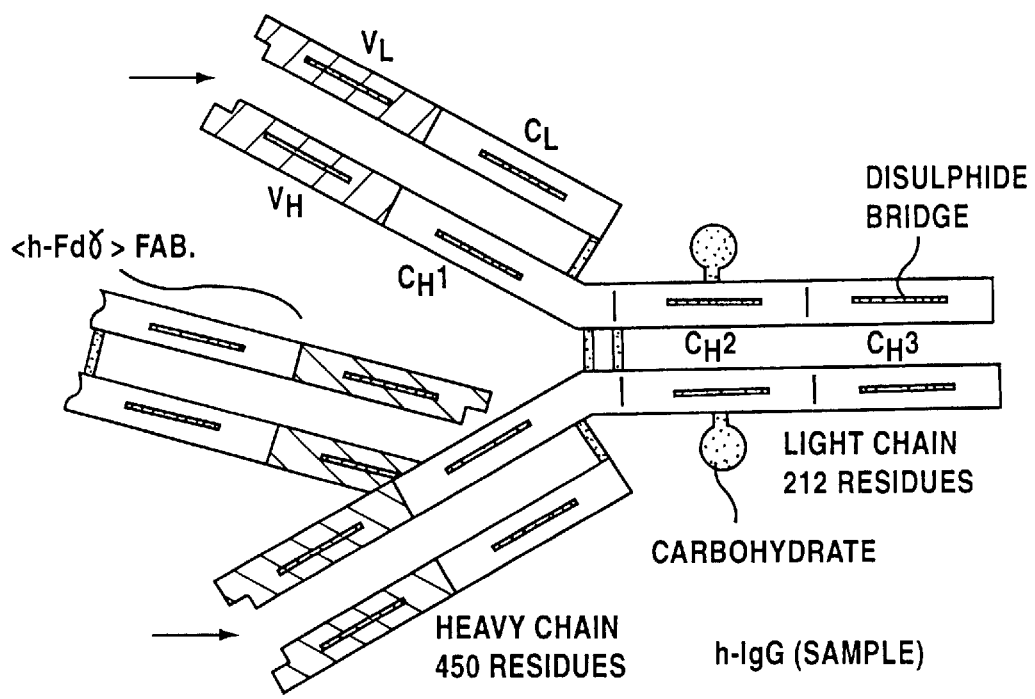

United States Patent [19]

Schlieper et al.

[11] Patent Number: 5,965,378

[45] Date of Patent: Oct. 12, 1999

[54] ANTIBODY CLASS-SPECIFIC INTERFERENCE ELIMINATING REAGENT

[75] Inventors: Dittmar Schlieper, Iffeldorf; Helmut Lenz, Tutzing; Urban Schmitt, Oberhausen; Volker Klemt, Weilheim, all of Germany

[73] Assignee: Roche Diagnostics GmbH, Mannheim, Germany

[21] Appl. No.: 08/809,412

[22] PCT Filed: Nov. 2, 1995

[86] PCT No.: PCT/EP95/04307

§ 371 Date: Apr. 24, 1997

§ 102(e) Date: Apr. 24, 1997

[87] PCT Pub. No.: WO96/14337

PCT Pub. Date: May 17, 1996

[30] Foreign Application Priority Data

Nov. 4, 1994 [DE] Germany ............................ 44 39 452

[51] Int. Cl.⁶ ..................................................... G01N 33/53
[52] U.S. Cl. .............................. 435/7.9; 435/7.1; 435/7.5; 435/962; 435/965; 436/506; 436/509; 436/512; 436/513; 436/518; 436/547; 436/548; 530/380; 530/387.1; 530/388.1; 530/388.15; 530/829; 530/861; 530/862; 530/863; 530/864; 530/865; 530/866

[58] Field of Search ................................ 435/7.1, 7.5, 7.9, 435/962, 965; 436/506, 509, 512, 513, 518, 547, 548; 530/380, 387.1, 388.1, 388.15, 829, 861, 862, 863, 864, 865, 866

[56] References Cited

U.S. PATENT DOCUMENTS 4,914,040   4/1990   Lenz et al. .

OTHER PUBLICATIONS

Carrel et al., Immunochemistry. 10:245–250, 1973.
Duermeyer et al., Journal of Medical Virology. 4:25–32, 1979.
McDougal et al., J. Lab. Clin. Med. 106(1):80–87, 1985.
Powell et al., The Journal of Rheumatology, An Improved Assay for IgG Rheumatoid Factor: Its Value in the Diagnosis of Rheumatoid Arthrits, 1985, pp. 427–731.

*Primary Examiner*—Christopher L. Chin
*Assistant Examiner*—Bao-Thuy Nguyen
*Attorney, Agent, or Firm*—Nikaido, Marmelstein, Murray & Oram LLP

[57] ABSTRACT

The invention concerns a composition composed of several different antibodies or/and antibody fragments which is suitable as a reagent to reduce interferences in an immunological method for the class-specific detection of antibodies from one or several of the immunoglobulin classes G, M, A, D and E.

22 Claims, 2 Drawing Sheets

ANTIBODY CLASS-SPECIFIC INTERFERENCE ELIMINATING REAGENT

The invention concerns a composition composed of several different antibodies or/and antibody fragments which is suitable as a reagent to reduce interferences in an immunological method for the class-specific detection of antibodies from one or several of the immunoglobulin classes G, M, A, D and E.

The mammalian organism contains various classes of antibodies which are formed by the B celli of the immune system to defend against antigens. The antibody molecules are each composed of one or several sets of four polypeptide chains, two heavy chains and two light chains which are linked together via disulfide bridges.

Antibodies are generally divided into the classes G, M, A, D and E. These five immunoglobulin classes differ in their heavy chain which is denoted $\gamma$, $\mu$, $\alpha$, $\delta$ and $\in$ chain. In addition there are also immunoglobulin subclasses in the case of IgG, IgA and IgM.

Antibodies of the IgG class constitute 70 to 75% of the total immunoglobulin in normal human serum (corresponding to 8 to 16 mg/ml). They are mainly formed as the secondary immune response of the organism to an infection.

Antibodies of the IgM class make up ca. 10% of the immunoglobulin present in human serum and have a pentameric structure. These antibodies appear very early after an infection so that their determination is important for the early detection of diseases.

The immunoglobulins of the IgA class form about 15 to 20% of the immunoglobulin present in human serum and are the most important secretory immunoglobulin in saliva, milk and secretions of the urogenital region.

Antibodies of the IgD class are located on the membrane of circulating B cells and it is assumed that they play a role in autoimmune diseases.

Antibodies of the IgE class only occur in a very small amount in serum, but they play an important role in a number of allergic reactions such as asthma and hay-fever.

The class-specific determination of immunoglobulins i.e. the selective determination of antibodies of one or several selected immunoglobulin classes or subclasses which are directed against a particular antigen in the presence of antibodies of other immunoglobulin classes or subclasses which are directed against the same antigen is of particular importance for the detection of particular diseases e.g. for the early diagnosis of infections, to differentiate between acute and healed infections and to make precise prognoses.

Methods for the class-specific determination of immunoglobulins are known. For this an immune component that is specific for a selected antibody class e.g. an antibody against the $\mu$ chain of human IgM can be coupled to a solid carrier and the antigen-specific immunoglobulin component can be detected by reaction with a directly or indirectly labelled antigen. A disadvantage of this type of method is that non-antigen-specific immunoglobulins of the respectively selected immunoglobulin class compete with the antigen-specific molecules for the solid phase antibodies. This can result in a falsification of the results dependent on this quantity ratio.

A further disadvantage of the methods of the state of the art is that a washing step is required after incubation of the sample with the immune components on the solid carrier and before reaction with the antigen-specific immune components. This is a potential source of error and considerably increases the testing time.

EP-B-0 292 810 discloses a method for the determination of antigen-specific antibodies from one of the immunoglobulin classes M, A, D and E in a sample liquid wherein an interference-eliminating reagent is added to avoid interferences by antibodies of the IgG class which is selected from anti-human IgG, aggregated human or animal IgG or a $\gamma$-Fc fragment. The interference-eliminating reagent is intended to eliminate the antigen binding of the specific IgG antibodies present in the sample and to suppress the activity of rheumatoid factors.

However, the reagents according to EP-B 0 292 810 for eliminating interference have some disadvantages. Thus insoluble immune complexes are produced which can lead to a turbidity in the sample and may interfere with the measurement. More importantly the disclosed reagents do not mask the antigen binding site of IgG so that even when sedimentation occurs there is still antigen binding and thus the test may still be falsified. Moreover when anti-human IgG antibodies are used the concentration of the reagent has to be adjusted exactly since an excess can lead to a dissolution of the precipitate.

The object of the present invention was to at least substantially avoid the disadvantages of the state of the art.

This object is achieved by providing a composition composed of several different antibodies or/and antibody fragments which is specific for the Fd section of the heavy chain of immunoglobulins of one or several of the classes IgG, IgM, IgA, IgD and IgE and at least substantially masks the ability of these immunoglobulins to bind antigens.

The anti-Fd reagent binds to that region of the heavy chain of the immunoglobulins to be masked which lies between the antigen binding site and the hinge region (in the region of the $V_H$ and the $C_H^1$ domain; cf. FIG. 1). The binding sites are preferably in the constant region of the $C_H^1$ domain of the immunoglobulins i.e. in the $C_{\alpha H}^1$, $C_{\delta H}^1$, $C_{\in H}^1$, $C_{\gamma H}^1$ and $C_{\mu H}^1$ region (cf. "Kurzes Lehrbuch der Immunologie", I. M. Roitt; Thieme Verlag, Stuttgart, New York (1987), chapter 5: "Antikbörper: Struktur und Funktion", p. 49 ff). Amino acid sequences of these domains are described for example in Kabat et al., Sequences of Proteins of Immunological Interest, 5th ed. (1992), U.S. Department of Health and Human Services, USA.

The action of the composition according to the invention is in particular that the presence of several different antibodies or antibody fragments which are directed towards different regions of the Fd section of a heavy chain masks the antigen binding capability of the antibodies concerned so strongly that they are no longer able to recognize the specific binding partners i.e. the antigens.

The composition is specific for the Fd section of the heavy chain i.e. it is essentially free of components which could react with the Fd section of a light chain i.e. a $\kappa$ or $\lambda$ chain. The maximum cross-reactivity with a light immunoglobulin chain is preferably $10^{-1}$ and particularly preferably $10^{-2}$ relative to the reactivity with the heavy chain.

The antibody or/and antibody fragment composition according to the invention can be added in a 5-fold molar excess relative to the antibody molecules that are to be masked whose ability to bind antigen is preferably inhibited by at least 50%, particularly preferably by at least 90% and most preferably by at least 99%.

The composition used according to the invention is preferably specific for a first immunoglobulin class selected from the classes IgG, IgM, IgA, IgD and IgE and has a maximum cross-reactivity with another immunoglobulin class of $10^{-2}$, particularly preferably $10^{-3}$ relative to the reactivity towards the first immunoglobulin class.

In a preferred embodiment of the invention the antibody or/and antibody fragment composition is specific for the Fd section of the heavy chain of immunoglobulin G in particular of human immunoglobulin G. This composition is suitable for the class-specific determination of antibodies from one or several of the classes IgM, IgA, IgD and IgE in the presence of antibodies of the IgG class. Such a composition preferably has a maximum cross-reactivity with another immunoglobulin class such as IgM of $10^{-2}$, particularly preferably $10^{-3}$ relative to the reactivity towards IgG.

Another preferred embodiment of the present invention is a composition which is specific for the Fd section of the heavy chain of immunoglobulins of the IgM class and can for example be used for the selective class-specific determination of antibodies of the IgG class.

For some applications it may be preferable for the composition to be species-specific for human immunoglobulin and have a maximum cross-reactivity with non-human immunoglobulin of $10^{-2}$, particularly preferably of $10^{-3}$ relative to the reactivity towards human immunoglobulin.

The composition used according to the invention is composed of antibodies or/and antibody fragments. The composition is preferably composed of monovalent antibody fragments e.g. Fab fragments which are obtainable by enzymatic cleavage of antibodies with papain and subsequent fractionation of the cleavage products. If a composition is used composed of monovalent antibody fragments this avoids sedimentation of the masked antibodies.

The composition according to the invention is composed of several different antibodies or/and antibody fragments which are each specific for different regions of the Fd section of the heavy immunoglobulin chain. The composition is preferably composed of polyclonal antibodies or/and antibody fragments, it can, however, also be composed of a mixture of at least two and preferably of at least three and particularly preferably of at least four different monoclonal antibodies or/and antibody fragments.

A polyclonal antibody or/and antibody fragment composition according to the invention is obtainable by a process in which (a) an experimental animal is immunized with an immunogen which contains the Fd section of the heavy chain of immunoglobulins from a first immunoglobulin class, (b) a polyclonal antiserum is obtained from the experimental animal, (c) the polyclonal antiserum is optionally converted by cleavage into monovalent antibody fragments, (d) the antiserum or the monovalent antibody fragments are subjected to one or several immunosorption steps which allow a selection for antibodies or/and antibody fragments which are specific for the Fd section of the heavy chain of the first immunoglobulin class and (e) an antibody or antibody fragment composition with a specificity for the Fd section of the first immunoglobulin class is isolated.

The use of a suitable immunogen in combination with carrying out suitable immunosorption steps enables an antibody or antibody fragment composition to be isolated which is specific for the Fd section of the heavy chain of one or several selected immunoglobulin classes and preferably has essentially no cross-reactivity with other immunoglobulin classes or immunoglobulins from a species that is foreign to that of the selected classes. Whole antibodies, antibody fragments such as antibody fragments produced by enzymatic cleavage such as Fab, Fab' or F(ab)'$_2$ or recombinant antibody fragments, peptide epitopes or mixtures thereof can for example be used as immunogens. The use of immunogens which are free of antibody Fc components is preferred. In this manner it is possible to substantially avoid the formation of anti-Fc antibodies in the experimental animal e.g. a sheep, a rabbit or a mouse.

The immunosorption steps of the process according to the invention preferably comprise (i) at least one positive immunosorption against an antigen which contains the Fd section of the heavy chain of the first immunoglobulin class and the isolation of binding components of the composition which specifically recognize the Fd section of the heavy chain of the first immunoglobulin class. If an immunogen is used which contains the Fd section of the heavy chain of immunoglobulin G e.g. an Fab fragment, the antiserum or the antibody fragments are subjected to a positive immunosorption against immunoglobulin G or fragments thereof which contain the Fd section. The use of Fc-free antigens e.g. Fab fragments is recommended in the positive immunosorption if a whole immunoglobulin has been used as the immunogen.

The immunosorption steps preferably additionally comprise (ii) at least one negative immunosorption against antigens or components thereof which are selected from immunoglobulin classes which are different from the first immunoglobulin class and the isolation of non-binding components of the composition. This negative immunosorption substantially reduces the cross-reactivity of the composition with the Fd section of the light chain and with the Fd section of the heavy chain of other immunoglobulin classes. In order to produce a composition that is specific for the Fd section of immunoglobulin G the negative immunosorption can be carried out against IgM, IgD, IgE or/and IgA or components thereof. If it is intended to produce an interference eliminating reagent for the selective determination of IgM in the presence of IgG, one or several immunosorption steps against IgM or components thereof are carried out Optionally the immunosorption steps can furthermore comprise (iii) at least one negative immunosorption against antigens which are selected from the first immunoglobulin class of a species which is different from the species of the immunoglobulins in the positive immunosorption step (i) or components thereof and the isolation of non-binding components of the composition. It is preferable to carry out this step when the composition is to be used later in an immunoassay in which a detection antibody is used of the same immunoglobulin class but from another species. Preferably the positive immunosorption (i) is carried out with human immunoglobulins and the negative immunosorption (iii) is carried out with immunoglobulins of a non-human species e.g. the mouse. When a composition is produced that is specific for the Fd section of human immunoglobulin G the negative immunosorption step (iii) is carried out against immunoglobulin G of a non-human species.

The immunosorption steps are preferably carried out by adsorption chromatography on columns which contain the antigens used in each case in an immobilized form. Procedures for obtaining purified antigen preparations and for immobilizing antibodies or antibody fragments on a carrier material are well-known to a person skilled in the art (cf for example EP-A-0 394 819 in particular example 7).

The antibody or/and antibody fragment composition according to the invention can be preferably used in an immunoassay for the selective class-specific determination of antibodies of the classes IgG, IgM, IgA, IgD or/and IgE in order to suppress the interferences caused by antibodies of other classes. For this a human serum or plasma sample which is to be measured in which it is intended to carry out a class-specific quantification of an antibody of a particular immunoglobulin class (e.g. IgM) which is directed towards a particular e.g. viral or bacterial antigen is for example admixed with an IgG-specific composition according to the invention preferably after a pre-dilution step so that the specific and unspecific IgG present in the sample is essentially completely masked and in the subsequent immunological detection only the IgM but not the IgG is detected in the sample. This enables a differential quantification of the specific content of a particular antibody class without interference by the specific content of another antibody class. The use of the composition according to the invention allows a one-step test procedure without a wash process.

Thus a subject matter of the present invention is also a method for the selective immunological detection of specific antibodies from one or several selected immunoglobulin classes in a sample liquid which also contains other immunoglobulin classes which is characterized in that the sample liquid is incubated with a composition according to the invention in order to suppress interferences caused by other immunoglobulin classes and then the presence or/and amount of the antibodies of the selected classes to be detected is determined in the sample liquid. The composition is preferably added in an amount which corresponds to an at least 5-fold molar excess of the active components compared to the antibodies of the other immunoglobulin classes present in the sample liquid i.e. the non-selected immunoglobulin classes. The composition is preferably added in a 10- to 1000-fold molar excess. The duration of the pre-incubation pre-incubation is preferably 5 to 60 min and particularly preferably 10 to 30 min.

It is particularly preferable to carry out the immunological test procedure for the determination of specific antibodies according to the principle of a heterogeneous immunoassay in the presence of a reactive solid phase and two receptors $R_1$ and $R_2$ capable of binding to the antibodies to be detected in which $R_1$ is bound to the solid phase or is capable of binding to the solid phase and $R_2$ is directly or indirectly labelled. The antibodies to be detected can then be determined, optionally after separating the solid phase and incubation liquid, by measuring the label in the solid phase or/and in the incubation liquid.

A conjugate of an antigen reacting specifically with the antibodies to be detected and a solid phase binding group can be used as the solid phase receptor $R_1$. In this case the receptor $R_2$ can either be an antigen reacting specifically with the antibodies to be detected or an antibody which recognizes the selected antibody class e.g. an anti-IgM antibody or an appropriate antibody fragment. The receptor $R_2$ can be directly or indirectly labelled i.e. it can be coupled to a labelling group or it can bind to a further receptor which in turn carries a labelling group.

It is also possible to use a conjugate of an antibody or an appropriate antibody fragment which recognizes the selected antibody class and a solid phase binding group as the solid phase receptor $R_1$. In this case an antigen which reacts specifically with the antibodies to be detected is used as the labelled receptor $R_2$.

One preferably uses a solid phase coated with streptavidin or avidin and a biotinylated receptor $R_1$ which can bind to this solid phase. Chromophore substances, radioactive isotopes, enzymes, NMR-labels or all other labels known from the state of the art can be used as the label. Luminescent metal complexes are preferably used in which the label can be measured by electrochemiluminescence. Examples of luminescent metal complexes and of methods and devices for the measurement of electrochemiluminescence are described in EP-A-0 199 804, EP-A-0 580 979, WO87/06706, WO90/05301, WO90/11511 and WO92/14138 to the disclosure of which reference is hereby made. Enzymes (e.g. peroxidase, alkaline phosphatase or β-galactosidase) are a further preferred label in which the label can be measured by detection of the respective enzymatic reaction.

Yet a further subject matter of the present invention is a reagent for the selective immunological detection of specific antibodies from one or several selected immunoglobulin classes which contains a composition according to the invention.

The invention is further elucidated by the following examples and figures.

Figure 2:
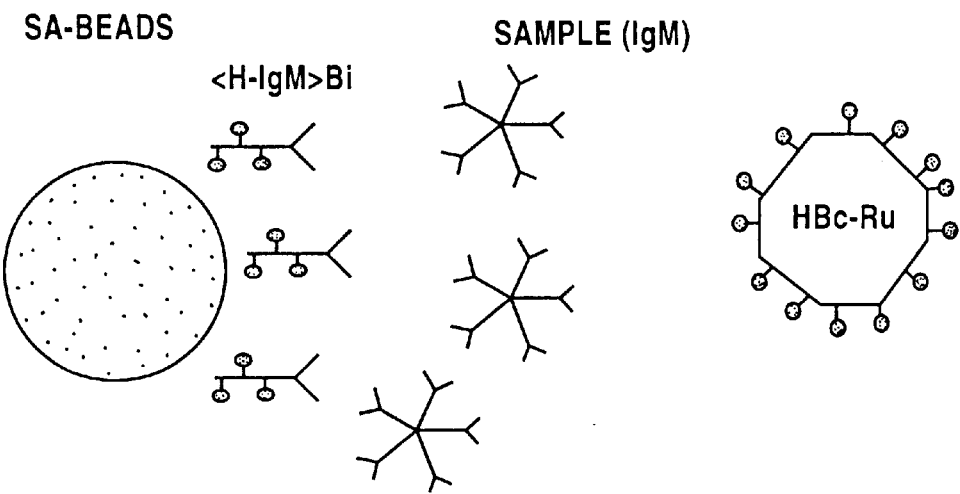
Figure 3:
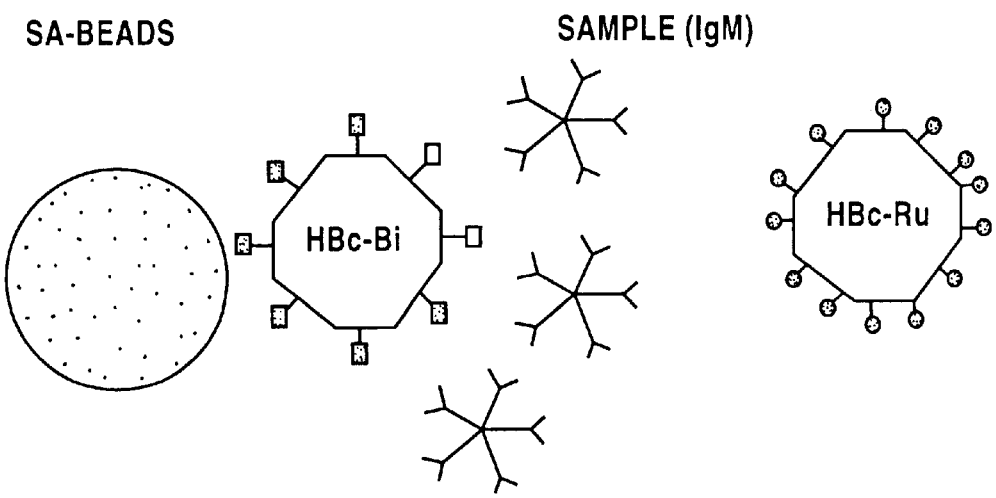

FIG. 1 shows the binding to human IgG (h-IgG) of an Fab fragment (<h-Fdγ>Fab) directed towards the Fd section of the heavy chain, FIG. 2 shows the test principle of the class-specific detection of anti-HBc IgM by electrochemi-luminescence carried out in example 4 and FIG. 3 shows a further test principle for a class-specific detection of anti-HBc IgM by electro-chemiluminescence.

EXAMPLE 1

Production of a Reagent according to the Invention 1.1 Production of the Immunogen The immunoglobulin G fraction is purified from human serum by conventional standard methods. This purification can for example be carried out by aerosil delipidation, precipitation with ammonium sulfate, chromatography on DEAE-Sepharose FF and optionally immunosorption on immobilized IgG-specific polyclonal antibodies.

The immunoglobulin fraction purified in this manner is cleaved with papain into Fab and Fc fragments. The cleavage is preferably carried out at pH 7 and at 37° C. with an IgG concentration of 10 mg/ml, 40 mU/ml papain, 7 and 10 mmol/l cysteine. The Fab parts are purified of the Fc parts by DEAE-Sepharose FF chromatography and gel chromatography (e.g. Sephacryl TSK S200 and S300). The Fab fragments are preferably coupled to a carrier protein e.g. maleimide-activated Keyhole Limpet Haemocyanine (Boehringer Mannheim, Biochemica Catalogue, Order No. 1376438) in order to increase the immune reaction. For this Fab fragments are firstly activated with N-succinimidyl-S-acetylthiopropionate (SATP) in a molar ratio of 1:6. The carrier protein is coupled with the activated Fab fragment in a molar ratio of 1:1.

Fab fragments of other immunoglobulin classes (e.g. Fabμ) can be produced in a corresponding manner.

1.2 Immunization of Sheep

Sheep are immunized by standard methods using the immunogen produced in example 1. In an immune reaction these form polyclonal antibodies against human Fab which are directed towards the light chain part as well as towards the heavy chain part of human Fab.

Crude serum is withdrawn from the immunized sheep and the IgG fraction is isolated from this by the methods that have already been described.

1.3 Production of an Fd-Specific Reagent

The sheep immunoglobulin G fraction is proteolytically cleaved with papain. The Fab fragments are separated from the other cleavage products by means of DEAE anion exchange chromatography.

The components that are directed towards the Fd section of the heavy chain are purified from the total sheep Fab fraction by several immunosorption steps.

The components that are directed specifically towards the light chain (κ or λ) of human IgG can be removed by an optional several-fold passage through an immuno-adsorber on which human IgM is immobilized because the constant region of the light chain of IgG and IgM is homologous. Whereas the components that are directed towards the light chain are adsorbed to the column, the components directed towards the Fd section of the heavy chain are located in the column eluant. A Spherosil column coupled with polyclonal IgM is used as the column. The application buffer is for example PBS/azide (50 mmol/l K-phosphate pH 7.5; 150 mmol/l NaCl; 0.1% sodium azide).

The non-binding fractions from the IgM column are pooled and subjected to a passage through a further immuno-adsorber which can optionally be repeated several times on which human IgG is immobilized. The specific fractions of anti-Fd sheep Fab can be separated on this column from unspecific sheep Fab fractions. The Fd-specific sheep Fab binds to this column and can be eluted with an elution buffer e.g. 1 mol/l propionic acid. The other components do not bind and are removed by washing the column with a suitable buffer (e.g. PBS/azide).

Furthermore interfering cross-reactivities with the mouse antibodies that are usually used in immunological tests as binding partners can be removed by an additional passage through an immuno-adsorber containing immobilized mouse IgG. The desired components of the preparation are in the column eluant.

The binding of an Fab fragment specific for human Fdγ (<h-Fdγ>Fab) to human IgG (h-IgG) is shown schematically in FIG. 1. The antigen binding sites of the h-IgG are in each case marked with arrows.

EXAMPLE 2

Examination of the Purity of the Reagent

Microtitre plates (MTP) from the Nunc Co. were coated with sheep Fab-specific rabbit IgG as a solid phase or capture antibody (10 μg/ml rabbit IgG, sodium carbonate buffer pH 9.6, re-coating with 1% bovine serum albumin in PBS buffer). The reagent to be analysed is pre-incubated as a sample with increasing concentrations (e.g. 0 to 10 μg/ml) in each case of a preparation of purified human Fabγ fragments or human Fabμ fragments and subsequently transferred to the coated MTP (sample volume 200 μl, incubated for 2 h at room temperature, buffer PBS containing 1% bovine serum albumin).

The sheep Fab components of the sample that are specific for human Fdγ are bound to the solid phase as are impurities that may be present which are directed towards the light immunoglobulin chain and which may not have been completely separated during the purification. Non-bound components are removed by washing three times with PBS buffer.

A horseradish peroxidase coupled to human Fabγ (200 μl, 50 mU/ml) is used as the detection reagent. After washing three times with PBS buffer the enzymatic activity of the bound peroxidase conjugate is developed by incubating for 1 h at room temperature with the substrate ABTS® and subsequently measured photometrically at 405 nm. Of the sheep Fab components of the sample that were previously bound to the solid phase only those components which are directed towards human Fab are detected by the enzyme marker conjugate. As a result a positive signal of 1000 to 3000 mA is produced in the control without addition of Fabμ and Fabγ. This corresponds to the total amount of the sheep Fab directed towards human Fab which is present in a preparation to be examined. In the samples to which increasing amounts of human Fabγ had been added, the masking of the Fdγ-specific sheep Fab results in an increasing displacement of the conjugate and thus to a measured signal curve which tends towards 0 or towards a blank value. In contrast in the samples to which increasing amounts of human Fabμ had been admixed only the sheep Fab components that are directed towards the light chain can be masked so that in this case a decrease in the signal only occurs when such undesired components are still present in the sheep Fab preparation. The difference between the two displacement curves would in the latter case correspond to the actual amount of Fdγ-specific sheep Fab in the preparation.

The measurement of the sample without added human Fabμ or Fabγ results in an absorbance of 1600 mA. The sample+Fabμ results in an absorbance of 1500 mA. The sample+Fabγ results in an absorbance of 150 mA.

EXAMPLE 3

Use of an Fd-Specific Interference Eliminating Reagent in an Enzyme Immunoassay In order to demonstrate the functionality of the anti-Fd γ antibody fragment preparation prepared in example 1 anti-Fdγ was added to a human serum sample which contained antibodies (<HBc>) directed towards the core antigen of hepatitis B virus (HBc antigen). Subsequently HBc antigen was added and incubated. The anti-HBc-specific IgG can now react with this antigen provided it has not been masked by anti-Fdγ. Subsequently excess IgG (specific for HBc antigen and unspecific) was separated by washing. The IgG bound to the HBc antigen can now be detected by a peroxidase-labelled anti-IgG which binds to the Fcγ part of IgG.

The test procedure was as follows:

The samples containing anti-HBc IgG were admixed with various amounts of anti-Fdγ and incubated for 30 minutes at room temperature. Subsequently the samples were diluted further with 40 mmol/l phosphate buffer, pH 7.4 to 1:100.

In a streptavidin-coated test vessel 20 μl of the diluted sample was added to 500 μl of a solution of biotinylated HBc antigen (10 μg/ml from the Enzymun-test® anti-HBc) and incubated for 10 min. Subsequently 500 μl of a conjugate of peroxidase and anti-IgG antibody (50 mU/ml from the Enzymuntest® anti-HCV) was added, incubated for 60 min and washed. Subsequently 1000 μl substrate solution (H$_2$O$_2$ (sodium perborate) 3.2 mmol/l from the Enzymuntest® anti-HCV) was added and incubated for 60 min. Finally the absorbance was determined on an ES600 analyzer (Boehringer Mannheim GmbH).

The results of this experiment are shown in table 1. It can be clearly seen that the anti-Fdγ composition according to the invention alters the ability of IgG to bind antigen to the extent that it can no longer bind.

TABLE 1

| Sample | Content <HBc> [U/ml] | Absorbance (A) when anti-Fdγ is added to an undiluted sample [mg/ml] | | | | |
|---|---|---|---|---|---|---|
| | | 0 | 10 | 50 | 100 | 200 |
| 0 | 0 | 0.07 | 0.06 | 0.05 | 0.04 | 0.03 |
| 1 | 22000 | 1.63 | 1.35 | 0.63 | 0.4 | 0.16 |
| 2 | 6000 | 0.91 | 0.82 | 0.56 | 0.25 | 0.07 |
| 3 | 12000 | 1.05 | 1.0 | 0.69 | 0.25 | 0.07 |

EXAMPLE 4

Class-Specific Detection of Anti-HBc IgM by Electrochemiluminescence

An apparatus was used for the measurement as described in WO90/05302. The test principle is shown in FIG. 2 and is based on the use of a biotinylated antibody that is specific for human IgG (<H-IgM>Bi) and a HBc antigen which is directly labelled with a ruthenium complex (HBc-Ru). Alternatively it is also possible to use an indirectly labelled HBc antigen (by binding a ruthenylated anti-HBc antibody). The ruthenium complex and the techniques used for coupling to the HBc antigen or to the antibody are described in EP-A-0 199 804.

A further test principle is shown in FIG. 3. It is based on the use of a biotinylated HBc antigen (HBc-Bi) and a ruthenium-labelled HBc antigen (HBc-Ru).

The procedure was as follows:

90 μl of a solution of unspecific human IgM (11 μg/ml) with or without 1000 μg/ml anti-Fdγ was admixed with 10 μl of 1:100 pre-diluted samples or standards and incubated for 9 min at 37° C.

Subsequently 100 μl of a solution which contained ruthenium-labelled HBc antigen and a biotinylated anti-human IgM antibody (IgG), and 50 μl streptavidin-coated magnetic particles (Dynal Co.) were added, the mixture was subsequently incubated for a further 9 min. at 37° C., then transferred with assay buffer (200 mmol/l phosphate, pH 6.8, 0.1% polydocanol, 0.1% Oxabon A, 160 mmol/l tripropylamine) into the measuring cell thermostated at 28° C. and measured there.

The IgM concentration in the samples was subsequently determined based on a calibration curve. The results in terms of concentration are shown in Table 2.

As can be seen in the Table the IgM concentrations measured in the samples are increased by the addition of anti-Fdγ so that the IgM concentration range measured in the enzmymun system (where no IgG interference occurs due to a washing step) is affected.

Note: The samples 1 to 4 contained 6000, 12000, 6900 and 4500 U/ml respectively HBc-specific IgG i.e. a considerable excess. The interference caused by IgG is eliminated by addition of Fdγ.

TABLE 2

| Sample | Enzymun <HBc>IgM [U/ml] | Flash <HBc>IgM without <FDγ> [U/ml] | Flash <HBc>IgM with <Fdγ> [U/ml] |
|---|---|---|---|
| 1 | 249 | 116 | 281 |
| 2 | 56 | 21 | 51 |
| 3 | 62 | 20 | 96 |
| 4 | 140 | 39 | 110 |

We claim:

1. Isolated composition consisting essentially of several different antibodies, antibody fragments, or antibodies and fragments thereof, which bind to the Fd section of the heavy chain of immunoglobulins from at least one of the classes IgG, IgA, IgD and IgE and at least partially inhibit the binding of any of said immunoglobulins to an antigen.

2. The isolated composition as claimed in claim 1, wherein
    it is specific for the Fd section of the heavy chain of immunoglobulin G.

3. The isolated composition as claimed in claim 1, wherein in a 5-fold molar excess relative to the immunoglobulins, it inhibits the ability of the immunoglobulins to bind antigens by at least 50%.

4. The isolated composition as claimed in claim 3, wherein in a 5-fold molar excess relative to the immunoglobulins it inhibits the ability of the immunoglobulins to bind antigens by at least 90%.

5. The isolated composition as claimed in claim 1, wherein
    it is specific for a first immunoglobulin class and has a maximum cross-reactivity with another immunoglobulin class of $10^{-2}$ relative to the reactivity towards the first immunoglobulin class.

6. The isolated composition as claimed in claim 5, wherein
    it is specific for IgG and has a maximum cross-reactivity with IgM of $10^{-2}$ relative to the reactivity towards IgG.

7. The isolated composition as claimed in claim 6, wherein
    it has a maximum cross-reactivity of $10^{-3}$.

8. The isolated composition as claimed in claim 1, wherein
    it is composed of monovalent antibody fragments.

9. The isolated composition as claimed in claim 1, wherein
    it is composed of Fab fragments.

10. The isolated composition as claimed in claim 1, wherein
    it is specific for human immuno-globulin and has a maximum cross-reactivity with non-human immunoglobulin of $10^{-2}$ relative to the reactivity towards human immunoglobulin.

11. The isolated composition as claimed in claim 1, wherein
    it is composed of polyclonal antibodies or/and antibody fragments.

12. Method for the selective immunological detection of specific antibodies from one or several selected immunoglobulin classes in a sample liquid which also contains antibodies of other immunoglobulin classes, wherein
    the sample liquid is pre-incubated with the isolated composition as claimed in claim 1 in order to suppress interferences caused by the other immunoglobulin classes and then the presence or/and amount of the antibodies of the selected classes to be detected is determined in the sample liquid.

13. Method as claimed in claim 12, wherein
    the isolated composition is added in an amount which corresponds to an at least 5-fold molar excess of the active components relative to the antibodies of the other immunoglobulin classes present in the sample liquid.

14. Method as claimed in claim 13, wherein
    the isolated composition is added in a 10-fold to 1000-fold molar excess.

15. Method as claimed in claim 12, wherein
    the pre-incubation is carried out for a period of 5 to 60 min.

16. Method as claimed in claim 12, wherein
    the determination is carried out according to the principle of a heterogeneous immunoassay in the presence of a reactive solid phase and two receptors $R_1$ and $R_2$ which bind to the antibodies to be detected, in which $R_1$ is bound to the solid phase or is capable of binding to the solid phase and $R_2$ is directly or indirectly labelled and the antibodies to be detected are determined by measuring the label in the solid phase or/and in the incubation liquid.

17. Method as claimed in claim 16, wherein
    a conjugate of an antigen which specifically reacts with the antibodies to be detected and a solid phase binding group is used as receptor $R_1$ and an antigen which specifically reacts with the antibodies to be detected is used as receptor $R_2$ which is directly or indirectly labelled.

18. Method as claimed in claim 16, wherein a conjugate of an antigen which specifically reacts with the antibodies to be detected and a solid phase binding group is used as receptor $R_1$ and an antibody which recognizes the selected antibody class and is directly or indirectly labelled or a corresponding antibody fragment is used as receptor $R_2$.

19. Method as claimed in claim 16, wherein a conjugate of an antibody or a corresponding antibody fragment which recognizes the selected antibody class and a solid phase binding group is used as receptor $R_1$ and an antigen which is directly or indirectly labelled and specifically reacts with the antibodies to be detected is used as receptor $R_2$.

20. Method as claimed in claim 16, wherein a reactive solid phase coated with streptavidin or avidin and a biotinylated receptor $R_1$ are used.

21. Method as claimed in claim 16, wherein a luminescent metal complex is used as the label and the label is measured by electrochemi-luminescence.

22. Method as claimed in claim 16, wherein an enzyme is used as the label and the label is measured by detection of an enzymatic reaction.

* * * * *